United States Patent [19]
Cuilleron et al.

[11] Patent Number: 5,653,750
[45] Date of Patent: Aug. 5, 1997

[54] ARTIFICIAL HEART VALVE

[75] Inventors: Jean Cuilleron, Saint Etienne; Eugéne Baudet, Merignac, both of France

[73] Assignee: Fabrique D'Implants Et D'Instrument Chirurgicaux Sarl, France

[21] Appl. No.: 405,433

[22] Filed: Mar. 16, 1995

Related U.S. Application Data

[63] Continuation of Ser. No. 104,455, Aug. 10, 1993.

[30] Foreign Application Priority Data

Aug. 11, 1992 [FR] France ................... 92 10088

[51] Int. Cl.$^6$ .................................................. A61F 2/24
[52] U.S. Cl. .......................................... 623/2; 623/900
[58] Field of Search .............................. 623/2, 900, 66

[56] References Cited

U.S. PATENT DOCUMENTS

| | | | |
|---|---|---|---|
| 4,173,606 | 11/1979 | Stoy et al. | 623/2 |
| 4,259,072 | 3/1981 | Hirabayashi et al. | 433/173 |
| 4,274,437 | 6/1981 | Watts | 623/2 |
| 4,308,624 | 1/1982 | Klawitter | 623/2 |
| 4,373,216 | 2/1983 | Klawitter | 623/2 |
| 4,443,894 | 4/1984 | Klawitter | 623/2 |
| 4,601,719 | 7/1986 | Totten | 623/2 |
| 4,822,353 | 4/1989 | Bokros | 623/2 |
| 4,863,458 | 9/1989 | Bokros | 623/2 |
| 5,002,567 | 3/1991 | Bona et al. | 623/2 |
| 5,061,278 | 10/1991 | Bicer | 623/2 |
| 5,152,785 | 10/1992 | Bokros et al. | 623/2 |
| 5,171,263 | 12/1992 | Boyer et al. | 623/2 |
| 5,178,631 | 1/1993 | Waits | 623/2 |
| 5,192,309 | 3/1993 | Stupka et al. | 623/2 |
| 5,236,449 | 8/1993 | Bokros et al. | 623/2 |
| 5,236,451 | 8/1993 | Borkos et al. | 623/2 |
| 5,246,453 | 9/1993 | Bokros et al. | 623/2 |

FOREIGN PATENT DOCUMENTS 2663533 12/1991 France .

Primary Examiner—John G. Weiss
Assistant Examiner—Bruce E. Snow
Attorney, Agent, or Firm—Eckert Seamans Cherin & Mellott

[57] ABSTRACT

The valve consists of a ring (1) enclosing hinged curved wings (2), the ring having diametrically opposite fixtures (1b–1c) designed to offset the means of hinging the wings so that in their maximum opened position of at least 85°, the latter only project beyond the plane of the ring by a small amount thus delimiting, in conjunction with the shape of the wings, three equivalent areas allowing a laminar, axial central flow, the means of hinging the said wings being integrated in the thickness of the ring so that the ends of the wings, at the level of fixtures (1b–1c), are spread apart thus delimiting a space which is completely unobstructed in order not to limit or interfere with the central flow. The ring (1) has an internal peripheral fixture (1a) suitable to provide a support surface corresponding to the external shaped edge (2b) of wings (2) in the closed position of the latter, thus creating a damping effect.

17 Claims, 3 Drawing Sheets

ARTIFICIAL HEART VALVE

This is a continuation of application Ser. No. 08/104,455 filed Aug. 10, 1993.

BACKGROUND OF THE INVENTION

The invention relates in particular to a valve of the type described in copending patent application Ser. No. 08/057,211, filed May 3, 1993, which is a continuation of application Ser. No. 07/718,605, filed Jun. 21, 1991, now abandoned.

Essentially, this type of heart valve consists of a ring which encloses hinged curved wings. The ring has diametrically opposite fixtures designed to offset the means of hinging the wings so that in their maximum opened position of at least 85°, the latter only project beyond the plane of the ring by a small amount thus delimiting, in conjunction with the shape of the wings, three equivalent areas allowing a laminar, axial central flow. The means of hinging the said wings are integrated in the thickness of the ring so that the ends of the wings, at the level of the fixtures, are spread apart, thus delimiting a space which is completely unobstructed in order not to limit or interfere with the central flow.

According to the invention, an attempt has been made to improve these basic characteristics. In particular, it became apparent that at the instant the wings close, the latter tap slightly against the internal periphery of the ring. Taking into account frequencies of beating and, consequently, the opening and closing cycle of the wings, this can produce wear in the area where the wings come into contact with the body of the ring.

In addition, at the level of this contact area, in the closed positions of the wings, i.e. when they press against the ring, this produces a reaction force which is transmitted directly at the level of the hinge axis. The effect of this reaction force acts on the hinging of the wings.

The invention intends to overcome these drawbacks in a simple, reliable, effective and rational manner.

One of the problems which the invention aims to solve is to eliminate any reaction force likely to act on the hinging of the wings on the one hand and to prevent any wear at the level of the ring on the other hand. The intention is therefore to prevent the forces generated when the wings close in the contact area with the ring, from stressing the hinge part of the wings and resulting in wear of the wings at the level of this contact area. It is important to obtain a damping effect intended to reduce noise and wear taking into account the problems of fluid flow efficiency without interfering with the flow of blood.

In order to solve such a problem, the ring has an internal peripheral fixture in the form of a hollow imprint which matches the external shape of the edge of the wing and of which the cross-section consists of a curved profile provided by moving the external edge of the wings to their closed position, thus creating an end-stop effect.

Another problem which the invention aims to solve is to provide an end stop in the maximum opened position of the wings in a simple and effective manner with the intention of rationalising manufacture.

Such a problem is resolved by the fact that the fixtures have means of locking the wings in their opened position in the form of a separately mounted pad fixed so that it projects beyond the internal surface of the ring between the hinge parts of the said wings.

Another problem which the invention aims to solve is to simplify the hinge of the wings on the corresponding parts of the ring. In this regard, it should be noted that the means of hinging the wings consist of parts having a male hemispherical shape at each end which project beyond the profile of each wing and fit in the matching hemispherical recesses.

According to the invention and making allowance for the problem to be solved, the hemispherical recesses are formed in separately mounted studs integrated in the thickness of the ring which act as a bearing.

Ideally, the studs are cylindrical and are fixed in the matching receptacles formed in the thickness of the ring.

Another problem which the invention aims to solve is to optimize the hinge torque.

Such a problem is solved by the fact that the studs are made of a monocrystalline ceramic (meaning formed from a single crystal and thereby exhibiting uniform properties throughout) or any other material having a low coefficient of friction.

Note that this solution of separately mounted bearing surfaces for hinging the wings is particularly useful for rationalising manufacture and for obtaining surface finishes of excellent quality. In addition, it is possible to select the most appropriate material which, in particular, may be different from the material of which the ring and/or wing is/are made.

BRIEF DESCRIPTION OF THE DRAWINGS

Further objects, characteristics and advantages of the present invention will be apparent from the following description, reference being made to the accompanying drawings in which.

DETAILED DESCRIPTION OF THE PREFERRED EMBODIMENTS

Figure 1:
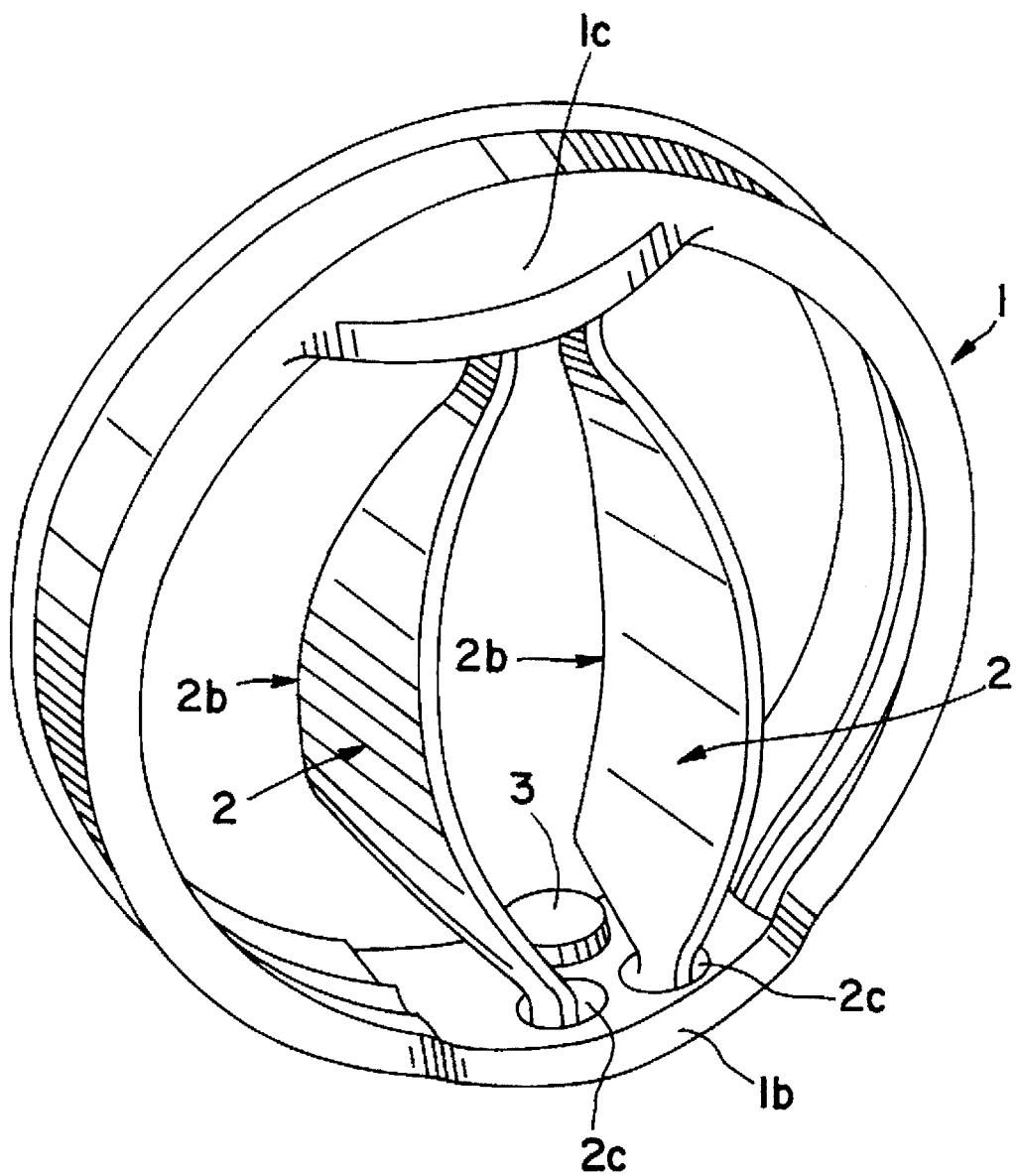
FIG. 1 is a perspective view of the heart valve according to the characteristics of the invention.

As shown in FIG. 1, the artificial valve consists of a ring (1) enclosing two identical hinged wings (2). The ring (1) has internal fixtures (1b) (1c) suitable to hinge the wings (2) in a maximum opened position and to delimit, in conjunction with the shape of the wings, three equivalent areas. These internal fixtures (1b) (1c) make it possible to integrate the wings inside the ring when the wings (2) are in their closed position.

To achieve this and as defined in applications Ser. No. 08/057,211, filed May 3, 1993, and Ser. No. 07/718,605, filed Jun. 21, 1991, these fixtures (1b) (1c) consist of two diametrically opposite parts formed directly so that they project beyond one of the surfaces of the ring on the inlet side of the valve. These parts (1b) (1c) offset the hinge mechanism of the wings (2) which, in the opened position, only project beyond the plane of the ring by a small amount.

Figure 2:
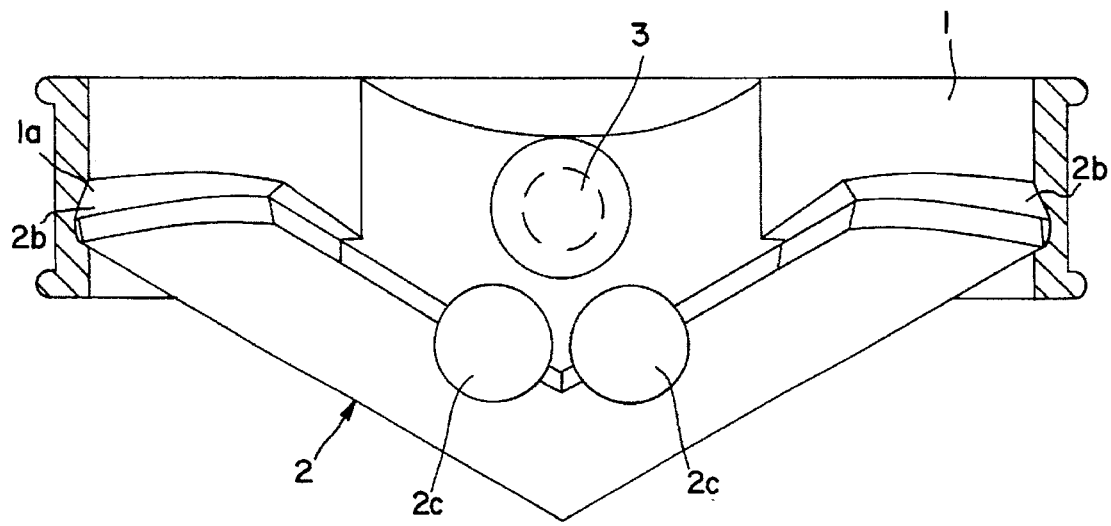
FIG. 2 is a large-scale partial cross-section showing the shape of the imprint formed in the internal periphery of the ring intended to cooperate with the profile of the wings in their closed position.

According to a basic characteristic of the invention the ring (1) has an internal peripheral fixture (1a) suitable to provide a linear support part or surface corresponding to the external shaped edge of the wings (2) in the closed position. This fixture is designed to create a damping effect and is intended to reduce noise and any wear. To achieve this, and as shown in FIG. 2, this fixture (1a) consists of a hollow imprint which matches the external shape of the edge (2b) of the wing (2). This imprint (1a) is formed either side of the hinge area of the wings (2). The cross-section of the imprint (1a) is created by the external shape of the wings when they pivot and move into the closed position, thus creating an end-stop effect.

Figure 3:
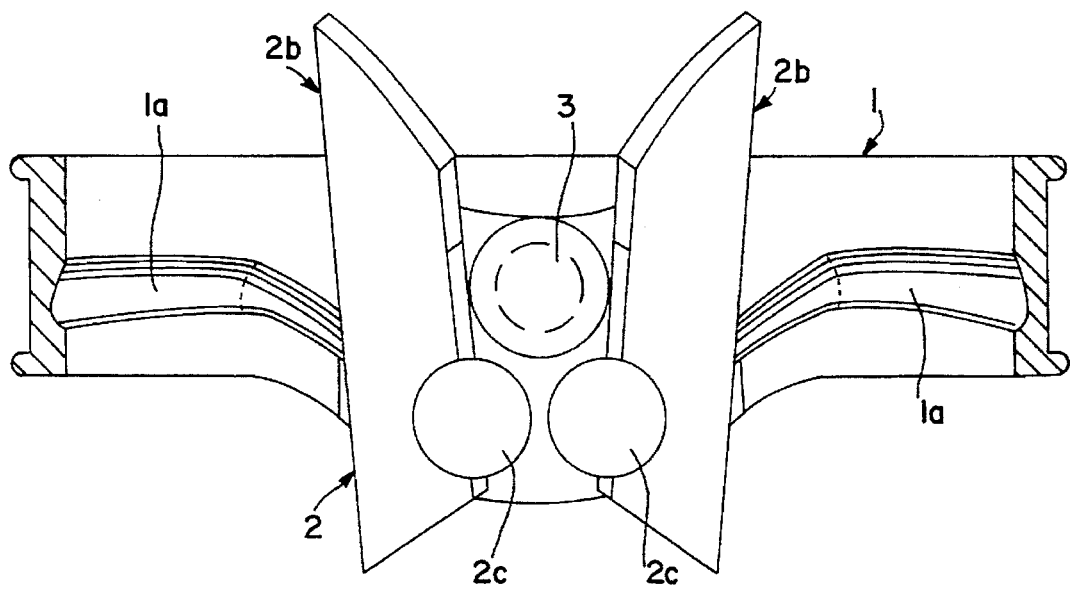
FIG. 3 is an equivalent view to FIG. 2 when the wings are in their opened position.
Figure 4:
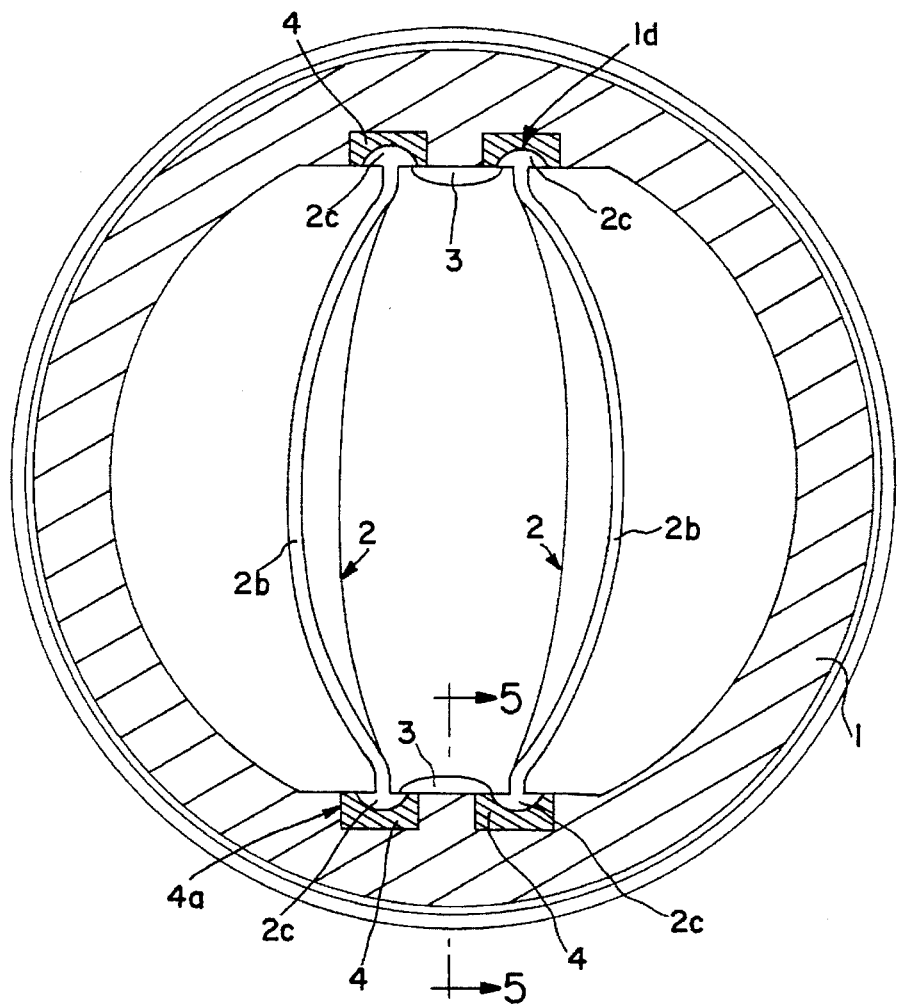
FIG. 4 is a large-scale cross section along line 4.4 in FIG. 1.
Figure 5:
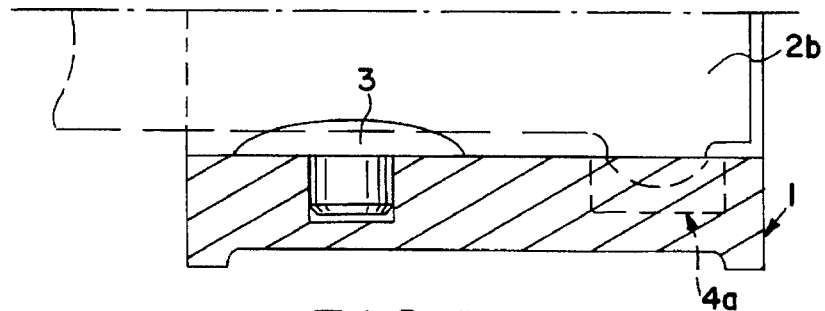
FIG. 5 is a large-scale cross-section along line 5.5 in FIG. 4.

According to another characteristic of the invention, the means of locking the wings in the opened position consist of a separately mounted discs (3). This discs is fixed so that it projects beyond the internal surface of the ring between the hinge parts of the wings (2). In particular, the discs (3) are separately mounted at the level of parts (1b) and (1c) of the ring (FIG. 3). The discs are made of the same material as that of the ring (1), namely titanium or a titanium alloy covered with a film of amorphous, isotropic carbon. Note that each of the discs (3) can be fixed on the ring by electron beam welding.

The hinge of each of the wings (2) at the level of parts (1b) and (1c) is provided by parts (2c) of male hemispherical shape at each end which are a direct extension of the edges of each wing. Each of the hemispherical parts (2c) is intended to cooperate with the matching hemispherical recesses in the ring (1). To achieve this, and according to another characteristic of the invention, the hemispherical recesses (4a) are formed in separately mounted studs (4) integrated in the thickness of the ring (1). The studs (4) are cylindrical and are fixed in matching receptacles (1d) formed in the thickness of the ring (1). Ideally, the studs (4) are made of a crystalline material or any other material with a low coefficient of friction, which makes it possible to optimize the hinge torque.

The advantages are apparent from the description.

We claim:

1. An artificial heart valve comprising:
    a ring in which curved wings are hinged, the ring having an inside wall and diametrically opposite hinge arrangements on the inside wall to offset from a plane of the ring a means for hinging the wings so that, in a maximum opened position of at least 85° to the plane of the ring, the wings only project slightly beyond the ring, the ring and the wings in the opened position defining between them three equal areas allowing a central axial and laminar flow, the means for hinging the wings being integrated in a thickness of the ring so that ends of the wings at the hinge arrangements are separated to define a completely free space in order not to limit and hinder the central flow; and,
    an internal peripheral recess defined by a pair of walls extending into the thickness of the ring and located on the inside wall to create inlet and outlet openings of equal diameter at opposite sides of the recess, the internal peripheral recess being complementary to an external edge profile of each said wing when in a closed position of the wing, the internal peripheral recess having a cross-section with a curved profile corresponding to movement of the external edge profile of the wings to the closed position, against which the edge of the wing is disposed in the closed position, and creating a stop for the wing.

2. The valve according to claim 1, further comprising means associated with the hinge fixtures for stopping the wings in the opened position, said means associated with the hinge fixtures including a disc which is inserted into a corresponding opening formed in the inside wall of the ring, the disc projecting from an internal surface of the ring to engage between hinging parts of the wings in the opened position.

3. The valve according to claim 1, wherein the means for hinging the wings comprises parts having a hemispherical projection at each end of each of the wings, which projects beyond a profile of each said wing and cooperate with complementary hemispherical recesses, and wherein the hemispherical recesses are formed in pads which are inserted in corresponding cavities formed in the inside wall of the ring, the cavities extending into the wall of the ring a distance less than the thickness of the ring.

4. The valve according to claim 3, wherein the pads are cylindrical and are fixed in complementary housings formed in the wall of the ring.

5. The valve according to claim 3, wherein the pads comprise a material having a low coefficient of friction.

6. The valve according to claim 5, wherein the pads comprise a monocrystalline ceramic.

7. An artificial heart valve comprising:
    a ring in which curved wings are hinged, the ring having an inside wall and diametrically opposite hinge arrangements on the inside wall to offset from a plane of the ring a means for hinging the wings so that, in a maximum opened position of at least 85° to the plane of the ring, the wings only project slightly beyond the ring, the ring and the wings in the opened position defining between them three equal areas allowing a central axial and laminar flow, the means for hinging the wings being integrated in a thickness of the ring so that ends of the wings at the hinge arrangements are separated to define a completely free space in order not to limit and hinder the central flow; and,
    means associated with the hinge arrangements for stopping the wings in the opened position, said means associated with the hinge arrangements including a disc which is inserted into a corresponding opening formed in the inside wall of the ring, the disk projecting from the inside wall of the ring to engage between hinging parts of the wings in the opened position; and
    a peripheral recess in the ring defined by a pair of walls extending into the thickness of the ring to form openings of equal diameter at opposite sides of the ring.

8. The valve according to claim 7, further comprising an internal peripheral fixture formed in the inside wall of the ring, the internal peripheral fixture having a hollow imprint which extends into the thickness of the ring and is complementary to an external edge profile of each said wing when in a closed position of the wing, the internal peripheral fixture having a cross-section with a curved profile corresponding to movement of the external edge of the wings to the closed position, against which the edge of the wing is disposed in the closed position, and creating a stop for the wing.

9. The valve according to claim 7, wherein the means for hinging the wings comprises parts having a hemispherical projection at each end of each of the wings, which projects beyond a profile of each said wing and cooperate with complementary hemispherical recesses, and wherein the hemispherical recesses are formed in pads which are inserted in corresponding openings formed in the inside wall of the ring, the cavities extending into the wall of the ring a distance less than the thickness of the ring.

10. The valve according to claim 9, wherein the pads are cylindrical and are fixed in complementary housings formed in the wall of the ring.

11. The valve according to claim 9, wherein the pads comprise a material having a low coefficient of friction.

12. An artificial heart valve comprising:

a ring in which curved wings are hinged, the ring having an inside wall and diametrically opposite hinge arrangements on the inside wall to offset from a plane of the ring a means for hinging the wings so that, in a maximum opened position of at least 85° to the plane of the ring, the wings only project slightly beyond the ring, the ring and the wings in the opened position defining between them three equal areas allowing a central axial and laminar flow, the means for hinging the wings being integrated in a thickness of the ring so that ends of the wings at the hinge arrangements are separated to define a completely free space in order not to limit and hinder the central flow wherein the means for hinging the wings comprises parts having a hemispherical projection at each end of each of the wings which projects beyond a profile of each said wing and cooperates with complementary hemispherical recesses, wherein mounting blocks are secured by force fit in corresponding cavities formed in the inside wall of the ring, the cavities extending into the wall of the ring a distance less than the thickness of the ring, the mounting blocks requiring no additional retaining means to remain in the cavities, and wherein the hemispherical recesses are formed in the mounting blocks.

13. The valve according to claim 12, wherein the mounting blocks are cylindrical and are fixed in complementary housings formed in the wall of the ring.

14. The valve according to claim 12, wherein the mounting blocks comprise a material having a low coefficient of friction.

15. The valve according to claim 12, further comprising an internal peripheral fixture formed in the inside wall of the ring, the internal peripheral fixture having a hollow imprint which extends into the thickness of the ring and is complementary to an external edge profile of each said wing when in a closed position of the wing, the internal peripheral fixture having a cross-section with a curved profile corresponding to movement of the external edge of the wings to the closed position, against which the edge of the wing is disposed in the closed position, and creating a stop for the wing.

16. The valve according to claim 12, further comprising means associated with the hinge fixtures for stopping the wings in the opened position, said means associated with the hinge fixtures including a disc which is inserted into a corresponding opening formed in the inside wall of the ring, the disk projecting from the inside wall of the ring and engaging between hinging parts of the wings in the opened position.

17. An artificial heart valve comprising:

a ring in which curved wings are hinged, the ring having an inside wall and diametrically opposite hinge arrangements on the inside wall to offset from a plane of the ring a means for hinging the wings so that in a maximum opened position of least 85° to the plane of the ring, the wings only project slightly beyond the ring, the ring and the wings in the opened position defining between them three equal areas allowing a central axial and laminar flow, the hinging means being integrated in a thickness of the ring so that ends of the wings at the hinge arrangements are separated to define a completely free space in order not to limit and hinder the central flow wherein each wing extends between an outer edge and a spaced inner edge, and between a pair of the hinging means as spaced apart from one another and positioned between the spaced inner and outer edges in respectively opposite positions;

each wing is shaped to define, between the spaced hinging means, a curved section-profile;

the outer edges having shapes determined by curved lines projected onto the curved profiles of the wings such that each outer edge defines a double-curved line;

each wing has, adjacent and substantially coextensive with the double-curved outer edge, marginal portions that define an abutment surface;

the ring has a thickness and in angularly spaced places the ring is recessed in from the inside wall to form a pair of generally spherical-wedge shaped recesses in the thickness of the ring, each spherical-wedge shaped recess being defined by generally a lune wall portion and a stop-surface wall portion, the wall portions extending into the thickness of the ring and at locations to create inlet and outlet openings of equal diameter at opposite sides of the recess;

each stop-surface wall portion being shaped to match and engage in close-joining contact the abutment surface which is coextensive with the double-curved outer edge of the respective wing, to stop movement of that wing in a closed position; and, each lune wall portion being shaped and arranged to permit closely spaced clearance of the outer edge of the respective wing as that wing moves reversibly to and from the closed position, whereby the wings while progressively approaching the closed position progressively cutoff the flow as the outer edges move transversely by the lune wall portions.

* * * * *